United States Patent [19]

Fournier et al.

[11] Patent Number: 5,776,601

[45] Date of Patent: Jul. 7, 1998

[54] TITANIA EXHAUST GAS OXYGEN SENSOR

[75] Inventors: Robert Gregory Fournier, Burton; Kailash Chandra Jain, Troy; Carlos Augusto Valdes, Flint, all of Mich.

[73] Assignee: General Motors Corporation, Detroit, Mich.

[21] Appl. No.: 742,609

[22] Filed: Oct. 28, 1996

[51] Int. Cl.$^6$ ................................................ B32B 18/00
[52] U.S. Cl. .................... 428/325; 428/328; 428/472; 428/701; 428/702
[58] Field of Search .................. 338/34; 73/23.31, 73/31.05; 428/325, 328, 472, 699, 701, 702

[56] References Cited

U.S. PATENT DOCUMENTS

| | | | |
|---|---|---|---|
| 4,228,128 | 10/1980 | Esper | 422/98 |
| 4,237,722 | 12/1980 | Achari | 73/23.31 |
| 4,469,626 | 9/1984 | Tuohig et al. | 252/514 |
| 4,532,492 | 7/1985 | Esper | 73/23.31 |
| 4,688,015 | 8/1987 | Kojima et al. | 338/34 |
| 4,720,394 | 1/1988 | Kojima et al. | 437/234 |
| 4,959,255 | 9/1990 | Suzuki et al. | 428/143 |

*Primary Examiner*—Timothy M. Speer
*Attorney, Agent, or Firm*—Lawrence B. Plant

[57] ABSTRACT

A titania exhaust gas oxygen sensor including an alumina substrate, thin-film electrodes deposited thereon, and a thick-film titania layer deposited atop the electrodes. The electrodes comprise a noble metal (e.g., platinum) having a plurality of titania particles dispersed throughout for promoting bonding to the titania, resistive layer when the titania layer is fired.

4 Claims, 1 Drawing Sheet

TITANIA EXHAUST GAS OXYGEN SENSOR

TECHNICAL FIELD

This invention relates to resistive-type, thick-film, titania, internal combustion engine exhaust gas oxygen sensors, and more particularly to titania-adherent electrodes therefor.

BACKGROUND OF THE INVENTION

Thick-film, titania, exhaust gas oxygen sensors are well known in the art, and comprise principally a sintered ceramic (e.g., alumina) substrate, a pair of thin-film electrodes which are bonded to the substrate and are resistant to attack by high temperature oxygen, and a layer of sintered titania engaging the electrodes. A thin-film heater may also be applied to the sintered alumina substrate in close proximity to the electrodes for controlling the temperature of the sensor. Such sensors are placed in the exhaust gas stream of an internal combustion engine, and are typically subjected to a temperature range of 260° C.–950° C.

Titania oxygen sensors fall into the category of "resistive-type" sensors which exchange oxygen with the exhaust gas which, in turn, results in resistivity changes within the $TiO_2$ as oxygen is added thereto or depleted therefrom. The change in resistivity of the $TiO_2$ is monitored, and used to measure the oxygen concentration in the exhaust gas. Such sensors are described in numerous publications including (a) U.S. Pat. No. 4,066,413, (b) U.S. Pat. No. 4,007,435, (c) U.S. Pat. No. 4,469,626, (d) U.S. Pat. No. 4,720,394, (e) U.S. Pat. No. 4,688,015, (f) the paper J. L. Pfeifer, T. A. Libsch and H. P. Wertheiner, "Heated Thick-Film Titania Exhaust Gas Oxygen Sensors," SAE Paper No. 840142, 1981, and the paper A. Takami, T. Matsuura, S. Miyata, K. Furusaki and Y. Wantanabe, "Effect of Precious Metal Catalyst on $TiO_2$ Thick Film HEGO Sensor with Multi-Layer Alumina Substrate," SAE Paper No. 870290, 1987, and the references cited therein.

$TiO_2$ oxygen sensors are typically made by the so-called "green tape" lamination method such as described in the aforesaid SAE Paper No. 870290. That method involves building-up the sensor by layering several sheets (i.e., tapes) of green ceramic material along with the electrodes, heater and $TiO_2$, and then firing the laminated structure. The green ceramic material comprises a ceramic powder distributed throughout a thermoplastic resin binder. The electrodes and heating element comprise oxidation resistant noble metals (e.g., Pt, Pd, alloys of Pt with Pd or Rh, etc.) which are screened onto, and sandwiched between the several lamina, and then heated to sinter the ceramic particles together, and to micromechanically bond the electrodes and heating element to the rough alumina surface resulting from the sintering. When Pt is used as the electrode/heater material, a reaction phase will be formed between the Pt and the $Al_2O_3$ if firing is above about 1500° C. This further promotes bonding with the $Al_2O_3$. Thereafter, a thick film of titania is deposited atop the electrodes, and fired to sinter the titania, to complete the sensor fabrication.

Unfortunately, the coefficients of thermal expansion and elastic moduli of the alumina and the titania differ sufficiently from each other that considerable thermal stresses being generated at the interface therebetween upon heating to exhaust gas temperatures. This, in turn, can lead to cracking, flaking or complete destruction of the titania film in some circumstances. Moreover, the titania does not adhere well to the thin-film electrode materials used heretofore which further contributes to poor bonding of the thick-film titania to the rest of the sensor.

SUMMARY OF THE INVENTION

The present invention contemplates a thick-film titania exhaust gas oxygen sensor having a thin-film electrode which contacts the titania and comprises titania particles embedded in a matrix of a noble metal (preferably Pt) which is resistant to oxygen attack at the operating temperature of the exhaust gas sensor. The electrode bonds well to both the alumina substrate and the titania resistive material, and acts as a buffer between the titania and the alumina to compensate for the differences in their respective coefficients of thermal expansion and elastic moduli. Tests have shown that adhesion between the titania resistive material, and Pt-$TiO_2$ electrodes made in accordance with the present invention is an order of magnitude higher than the adhesion between titania thick-film sensor material and titania-free Pt electrodes used heretofore.

BRIEF DESCRIPTION OF THE DRAWINGS

The invention will better be understood when considered in the light of the following detailed description of a specific embodiment thereof which is given hereafter in conjunction with the several figures in which.

DESCRIPTION OF THE PREFERRED EMBODIMENT

Figure 1:
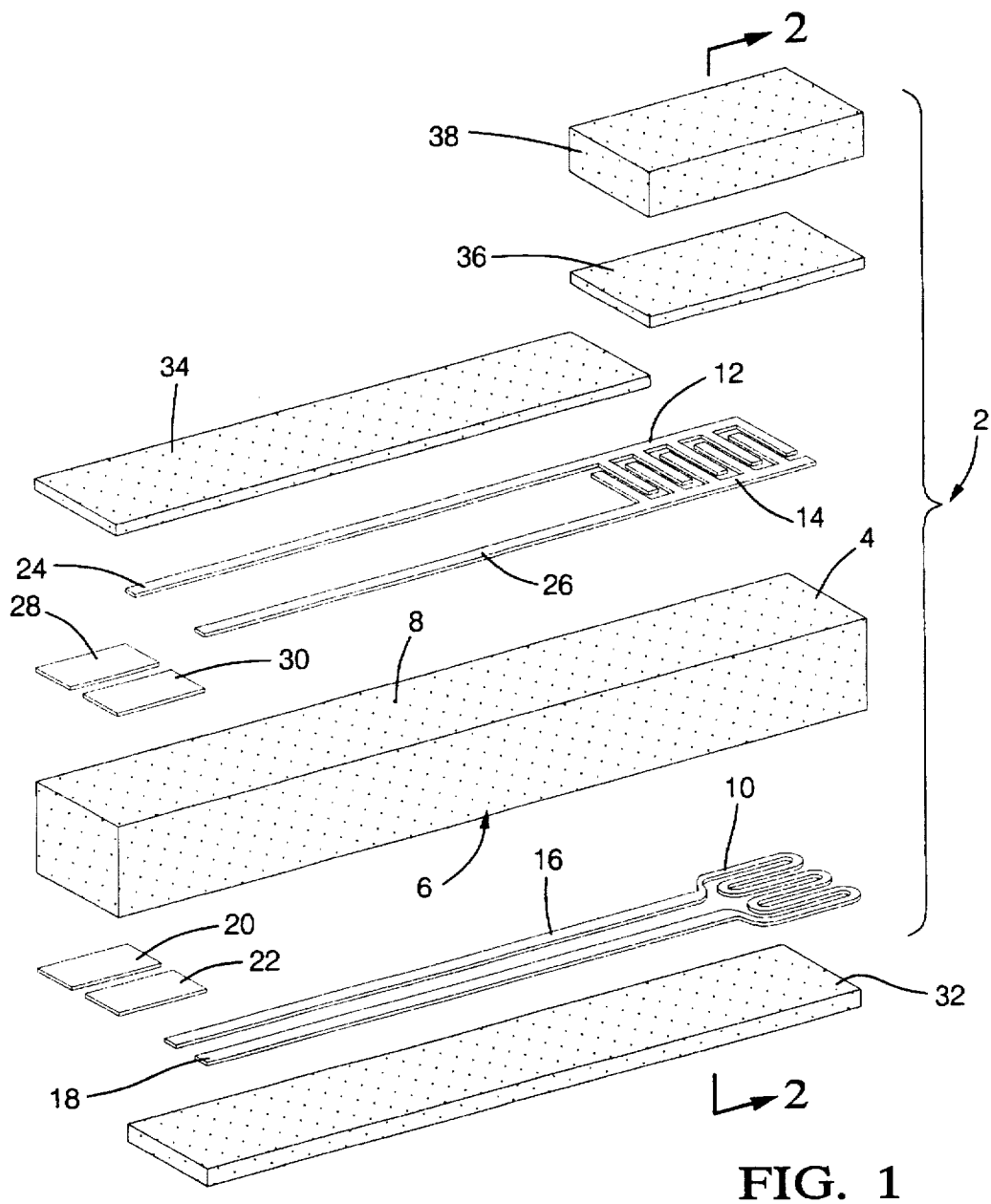
FIG. 1 is an exploded, perspective view of a green-tape type, titania oxygen sensor.
Figure 2:
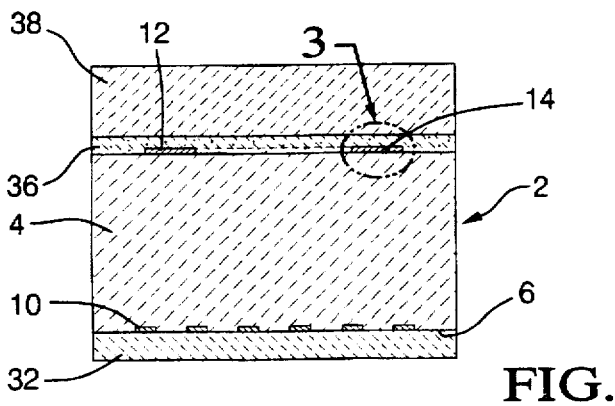
FIG. 2 is a sectional view in the direction 2—2 through the sensor of FIG. 1 after the several components have been assembled and fired.
Figure 3:
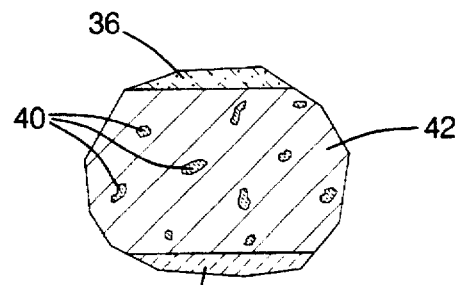
FIG. 3 is a magnified view of the electrode 14 of FIG. 2.

The Figures depict an oxygen sensor 2 comprising a sintered alumina body 4 having a first surface 6 on the underside thereof, and a second surface 8 on the topside thereof. A heating element 10 is formed on the body 4 by screening a metallic ink (e.g., platinum) onto the first surface 6. As is common practice, the Pt heating element 10 may also include some $Al_2O_3$ particles and/or some rhodium particles admixed therein to control the resistivity of the element and hence its effectiveness as a heater. Likewise, electrodes 12 and 14 are formed atop the body 4 by screening the metallic ink of the present invention onto the surface 8. Electrical leads 16 and 18 extend from the heating element 10 to electrical contact pads 20 and 22 which are connected to appropriate external wiring for applying heating current to the heating element 10. Similarly, electrical leads 24 and 26 extend from electrodes 12 and 14 respectively and engage electrical contact pads 28 and 30 for coupling the sensor 2 to external circuitry for measuring any voltage change that occurs between the electrodes 12 and 14. A protective layer of alumina 32 covers the heater 10 and associated electrical leads 16, 18. Similarly, a protective layer of sintered ceramic 34 covers the electrical leads 24 and 26. The protective layer 34 is shorter than the length of the substrate 4 so as to leave the electrodes 12 and 14 exposed on the surface of the substrate 4. The aforesaid components are laminated together and sintered in air for about 10 hrs. to about 20 hrs. at a temperature of about 1400° C. to about 1500° C. to bond them all together.

The base 4 and protective layers 32 and 34 comprise resin bonded alumina particles in the form of flexible tape, and are assembled using the well known green tape, co-firing lamination technology which is commonly used to assemble such $TiO_2$ sensors as well as barium titanate capacitors and similar devices. The "green tape" used to form the alumina lamina 4, 32 and 34 will typically comprise about 14% organic binder, a plasticizer, and the balance alumina particles having an average particle size of about 0.3 microns. Any of a variety of resin binders well known to those skilled in the art, may be used to form such tape. A thermoplastic polyacrylic emulsion which is sold commercially under the tradename RHLOPLEX-B-50-A® is a preferred such binder. Similarly, any plasticizer well known to those skilled in the art may be used, but is preferably alkylaryl polyether alcohol which is sold commercially under the tradename TRITON X-100® is preferred because it also functions as an emulsifier and stabilizer.

Following the sintering of the layers 4, 32 and 34 together, a thick film of titania particles 36 is screened over the electrodes 12 and 14. As screened, the film 36 will typically comprise about 65% by wt. particles (i.e., ca. 0.5–5 μm), and the balance a binder such as ethyl cellulose. Finally, a layer of porous ceramic (e.g., $TiO_2$) 38 is laid atop the titania layer 36 to protect the layer 36 from direct exposure to the exhaust gases, the pores in the layer 38 for $O_2$ exchange with the $TiO_2$ 36 to occur. The titania layer 36 may contain some catalyst (e.g., platinum) as is well known in the art and discussed in the aforesaid SAE Paper No. 870290. Thereafter, the assembly 2 is re-fired in air for about 10 min. to about 360 min. (preferably 60 min.) at about 1100° C. to about 1300° C. (preferably 1200° C.) to bond the titania layer 36 to the previously fired assembly.

In accordance with the present invention, the electrodes 12 and 14 will comprise a noble metal matrix (preferably Pt), and a sufficient amount of titania particles therein to promote improved bonding of the titania layer 36 to the electrodes 12 and 14 upon firing of the sensor. The electrodes will preferably contain about 10% to about 20% by weight $TiO_2$ particles in the size range of about 2–5 microns. The precise mechanism whereby improved bonding of the $TiO_2$ 36 to the electrodes 12 and 14 is not known. It is believed that titania particles 40 embedded in the noble metal matrix 42 of the electrode ink fuse to the titania layer 36 which, in turn, causes mechanical anchoring of the layer 36 to the electrodes 12 and 14. Moreover, the reduction in surface area provided by the Pt-$TiO_2$ electrode material during sintering is seen to also promote better adhesion. Finally, the mismatch in thermal expansion of Pt and $TiO_2$ crystal structures may provide some additional strengthening resulting from compressive stresses formed thereby.

In addition to achieving greater $TiO_2$-electrode adhesion, the metal-$TiO_2$ electrode material apparently also functions as a buffer between the alumina substrate 4 and the titania layer 36 and serves to ameliorate the stresses therebetween caused by the differences between their respective coefficients of thermal expansion and elastic moduli, and thereby reduce the propensity of the titania layer 36 to delaminate from the body 4.

Sensors made in accordance with the present invention will typically have a body portion 4 ranging in thickness from about 500 microns to about 1000 microns with about 750 microns being preferred. The protective layers 32 and 34 will vary in thickness from about 100 microns to about 140 microns, and the heater 10 and electrodes 12 and 14 will vary in thickness from about 12 microns to about 25 microns. The contact pads 20, 22, 28 and 30 will have a thickness of about 20 microns to about 50 microns and the thick-film titania layer 36 will have a thickness vary between about 40 microns to about 100 microns. The porous protective ceramic coating 38 will have a thickness of about 200 microns to about 400 microns. The drawings herein depict a sensor wherein the thicknesses of the various elements reflect the average thickness for each components as set forth above. However, in practice, the relative thickness of each may vary considerably.

Adhesion strength was determined by a "stud-pull" wherein aluminum pins, having a tip diameter of 3.58 mm and pre-coated with an epoxy, are bonded to the film by curing the epoxy adhesive at 150° C. The pin is used to pull the film from the substrate. The adhesive strength of the film is calculated as the force required to pull the film from the substrate divided by the area of the tip of the pin. Typically 6–10 pulls are made on each sample for a given condition.

Tests conducted in the course of this work revealed that adhesion between $TiO_2$ and Pt electrodes was low, and did not improve much with temperature. SEM and optical microscopic analysis of the fracture surfaces showed that while $TiO_2$ begins to sinter around 1050° C., if sintering temperatures were increased to about 1200° C., the failure mode shifted from cohesive failure (i.e., w/i the $TiO_2$ itself) to total adhesive failure (i.e., at the Pt-$TiO_2$ interface). In each case, the adhesive strength remained low. Similar tests conducted using $Al_2O_3$-containing Pt electrode inks showed the same type of total adhesive failure, and low adhesive strength. Similar tests were then conducted with $TiO_2$ particles added to the pure Pt electrodes. The $TiO_2$ particle addition to the pure Pt electrodes resulted in a combined adhesion/cohesion-type failure, and adhesion/cohesion strengths were ten times higher than for the pure Pt. Finally, it was observed that $TiO_2$ additions to the Pt electrode improved adhesion to the $Al_2O_3$ substrate by about 20%.

The aforesaid tests were conducted using inks with from 4 to 1 (4:1) to 19 to 1 (19:1) Pt to $TiO_2$ (Pt:$TiO_2$) weight ratios. The organics comprise 25%–50% by weight of the total ink composition. Ethyl cellulose, the binder, is 8% of the total organics, and terpineol, the solvent, is the other 92% by weight. These inks were screened-printed onto green $Al_2O_3$ substrate tapes such as described above, and fired in air at 1500° C. After firing, the electrodes comprised, by weight, 80–95% Pt, and 5–20% $TiO_2$. Thereafter, $TiO_2$ films (i.e., 50 μm thick) were screen printed onto the electrodes, and fired at 1200° C.

While the invention has been disclosed primarily in terms of a specific embodiment thereof, it is not intended to be limited thereto but rather only to the extent set forth hereafter in the claims which follows.

We claim:

1. In a resistive, thick-film, titania, engine exhaust gas oxygen sensor comprising principally a sintered alumina substrate, a thin-film electrode bonded to said substrate, and a layer of sintered titania supported on said substrate in contact with said electrode, the improvement wherein said electrode comprises (i) a noble metal resistant to oxidation at the operating temperature of said exhaust gas, and (ii) a sufficient amount of titania particles to promote bonding of said titania layer to said electrode upon firing of said titania layer.

2. An oxygen sensor according to claim 1 wherein said noble metal comprises platinum.

3. An oxygen sensor according to claim 1 wherein said electrode comprises about 10 to about 20 percent by weight titania particles.

4. An oxygen sensor according to claim 1 wherein said particles vary in size from about 0.5 to about 5 micrometers.

* * * * *